United States Patent [19]

Collins et al.

[11] 4,302,462

[45] Nov. 24, 1981

[54] 4(OR 3)-(3,4-DIHYDROXYPHENYL)PYRIDINES, THEIR CARDIOTONIC USE AND CARDIOTONIC USE OF THEIR METHYL ETHERS

[75] Inventors: Joseph C. Collins, East Greenbush; George Y. Lesher, Schodack; Baldev Singh, East Greenbush, all of N.Y.

[73] Assignee: Sterling Drug Inc., New York, N.Y.

[21] Appl. No.: 175,283

[22] Filed: Aug. 4, 1980

Related U.S. Application Data

[63] Continuation-in-part of Ser. No. 105,851, Dec. 20, 1979, abandoned.

[51] Int. Cl.$^3$ .................. C07D 213/30; A61K 31/44
[52] U.S. Cl. ...................................... 424/263; 546/344
[58] Field of Search .......................... 546/344; 424/263

[56] References Cited

U.S. PATENT DOCUMENTS 3,575,985  4/1971  Ritchie et al. ...................... 546/344

OTHER PUBLICATIONS

Ginos et al., Journal of Medicinal Chemistry, vol. 18, No. 12, pp. 1194–1200, (1975).
Coates et al., Journal of the Chemical Society, London, 1943, pp. 406–413.

*Primary Examiner*—Alan L. Rotman
*Attorney, Agent, or Firm*—Robert K. Bair; B. Woodrow Wyatt

[57] ABSTRACT

4(or 3)-(3,4-Dihydroxyphenyl)pyridine, a cardiotonic agent, is prepared by demethylating 4(or 3)-(3,4-dimethoxyphenyl)pyridine, preferably by heating with aqueous hydrogen bromide. 4(or3)-[3,4-di-(OR)-phenyl]-pyridine, where R is hydrogen or methyl, or pharmaceutically-acceptable acid-addition salt thereof is disclosed as the active component in a cardiotonic composition for increasing cardiac contractility and in the method for increasing cardiac contractility in a patient requiring such treatment. The novel isomeric 2-[3,4-di-(OR)-phenyl]pyridine, where R is hydrogen or methyl, is shown for comparative purposes.

5 Claims, No Drawings

4(OR 3)-(3,4-DIHYDROXYPHENYL)PYRIDINES, THEIR CARDIOTONIC USE AND CARDIOTONIC USE OF THEIR METHYL ETHERS

CROSS-REFERENCE TO RELATED APPLICATION

This application is a continuation-in-part of copending application Ser. No. 105,851, filed Dec. 20, 1979, and now abandoned.

BACKGROUND OF THE INVENTION a. Field of the Invention

This invention relates to dihydroxyphenylpyridines, intermediate dimethoxyphenylpyridines, their preparation and their use as cardiotonics.

b. Description of the Prior Art 4-(3,4-Dimethoxyphenyl)pyridine, inter alia, is shown in A. C. Ritchie U.S. Pat. No. 3,575,985, issued Apr. 20, 1971, as an intermediate in the preparation of 4-(3,4-dimethoxyphenyl)-1-methylpyridinium iodide, which was heated with aqueous hydrogen bromide in acetic acid to form a mixture of 4-(3,4-dihydroxyphenyl)-1-methylpyridinium iodide and bromide. The iodide-bromide mixture was treated with freshly prepared silver chloride to produce 4-(3,4-dihydroxyphenyl)-1-methylpyridinium chloride. The pyridinium salts of U.S. Pat. No. 3,575,985 were said to have "an effect upon the cardiovascular and nervous systems for example possessing antihypertensive activity and able to block or stimulate antonomic ganglia".

4-(3-Hydroxyphenyl)pyridine is shown, inter alia, by Coates et al. [J. Chem. Soc. 1943, 406].

Ginos et al. [J. Med. Chem. 18, 1194 (1975)] show, as an intermediate, 2-(3,4-dihydroxybenzyl)pyridine.

SUMMARY OF THE INVENTION

In a composition aspect, the invention resides in the compound 4(or 3)-(3,4-dihydroxyphenyl)pyridine or salt thereof, useful as a cardiotonic agent.

In a process aspect, the invention comprises treating 4(or 3)-(3,4-dimethoxyphenyl)pyridine with a demethylating agent to produce 4(or 3)-(3,4-dihydroxyphenyl)pyridine.

Another composition aspect of the invention relates to a cardiotonic composition for increasing cardiac contractility, said composition comprising a pharmaceutically-acceptable carrier and, as the active component thereof, the cardiotonic 4(or 3)-[3,4-di-(RO)-phenyl]pyridine or salt where R is hydrogen or methyl.

In a method aspect, the invention relates to a method for increasing cardiac contractility in a patient requiring such treatment which comprises administering to such patient an effective amount of a cardiotonic 4(or 3)-[3,4-di-(RO)-phenyl]pyridine or salt where R is hydrogen or methyl.

DETAILED DESCRIPTION INCLUSIVE OF PREFERRED EMBODIMENTS

In a composition aspect, the invention resides in 4(or 3)-(3,4-dihydroxyphenyl)pyridine or pharmaceutically-acceptable acid-addition salt thereof.

In a process aspect, the invention resides in the process which comprises reacting hydrogen bromide with 4(or 3)-(3,4-dimethoxyphenyl)pyridine to produce 4(or 3)-(3,4-dihydroxyphenyl)pyridine.

Another composition aspect of the invention resides in the cardiotonic composition for increasing cardiac contractility, said composition which comprises a pharmaceutically-acceptable pharmaceutical carrier and, as the active component thereof, an effective amount of the cardiotonic 4(or 3)-[3,4-di-(OR)-phenyl]pyridine or pharmaceutically-acceptable acid-addition salt thereof, where R is hydrogen or methyl. Preferred embodiments of this aspect of the invention are the compositions having, as the active component, said compund where R is hydrogen or said salt thereof.

A method aspect of the invention resides in the method for increasing cardiac contractility in a patient requiring such treatment which comprises administering to such patient an effective amount of the cardiotonic 4(or 3)-[3,4-di-(OR)-phenyl]pyridine or pharmaceutically-acceptable salt thereof, where R is hydrogen or methyl, a preferred embodiment being the method using said compound where R is hydrogen.

The 4(or 3)-[3,4-di-(OR)-phenyl]pyridine is useful both in the free base form and in the form of acid-addition salts, and, both forms or within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribably to the anions. In practicing the invention, it is convenient to form the hydrobromide or lactate. However, other appropriate pharmaceutically-acceptable salts within the scope of the invention are those derived from mineral acids such as hydrochloric acid, sulfuric acid, phosphoric acid and sulfamic acid; and organic acid such as acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structure of 4(or 3)-[3,4-di-(OR)-phenyl]pyridine was assigned on the basis of evidence provided by infrared, ultraviolet, nuclear magnetic resonance and mass spectra, by chromatographic mobilities, by the correspondence of calculated and found values for the elementary analyses, and, by methods of its preparation.

The manner of making and using the instant invention will now be generally described so as to enable a person skilled in the art of pharmaceutical chemistry to make and use the same, as follows.

The reaction of 4(or 3)-(3,4-dimethoxyphenyl)pyridine with a demethylating agent to produce 4(or 3)-(3,4-dihydroxyphenyl)pyridine was conveniently carried out by heating the reactants at about 100° to 126° C., preferably using aqueous hydrogen bromide. Alternatively, other demethylating agents can be used, e.g., hydrogen iodide, pyridine hydrochloride, boron tribromide, anhydrous aluminum chloride or bromide, or the like.

The intermediate 4(or 3)-(3,4-dimethoxyphenyl)pyridine is prepared by known or conventional means, as illustrated hereinbelow.

The following examples will further illustrate the invention without, however, limiting it thereto.

EXAMPLE 1

4-(3,4-Dihydroxyphenyl)pyridine, alternatively named 4-(4-pyridinyl)-1,2-benzenediol - A mixture containing 10.3 g. of 4-(3,4-dimethoxyphenyl)pyridine and 75 ml. of 48% hydrogen bromide was heated under reflux for five hours and then allowed to stand at room temperature over the weekend. The yellow crystalline precipitate was collected, washed with ethanol and dried in an oven at 95° C. to produce, as yellow needles, 11.8 g. of 4-(3,4-dihydroxyphenyl)pyridine hydrobromide, m.p. 214°–217° C.

4-(3,4-Dihydroxyphenyl)pyridine in free base form is obtained by treating an aqueous solution of its hydrobromide salt with excess aqueous sodium bicarbonate solution and collecting the free base form by filtration, first distilling off some of the excess water if necessary. Other acid-addition salts of 4-(3,4-dihydroxyphenyl)pyridine are conveniently prepared by adding to a mixture 0.5 g. of 4-(3,4-dihydroxyphenyl)pyridine in about 10 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., methanesulfonate, sulfate, phosphate, respectively. Also, the acid-additon salt of 4-(3,4-dihydroxyphenyl)pyridine is conveniently prepared in aqueous solution by adding to water with stirring molar equivalent quantities each of 4-(3,4-dihydroxyphenyl)pyridine and the appropriate acid, e.g., lactic acid or hydrochloric acid, to prepare respectively the lactate or hydrochloride salt of 4-(3,4-dihydroxyphenyl)pyridine in aqueous solution.

The intermediate 4-(3,4-dimethoxyphenyl)pyridine and its isomeric 3-(3,4-dimethoxyphenyl)pyridine and 2-(3,4-dimethoxyphenyl)pyridine were prepared as follows. To a stirred mixture cooled in an ice-salt bath and containing 200 g. of 4-aminoveratrole, 400 ml. of concentrated hydrochloric acid and 100 ml. of water was added a solution containing 102 g. of sodium nitrite in 180 ml. of water over a two hour period, while maintaining a reaction temperature below 5° C. during this addition. The reaction mixture was stirred further for an additional fifteen minutes and then added slowly over a period of about two and one-half hours to 2 l. of stirred pyridine preheated to 40° C., keeping the internal temperature between 45°–55° C. The mixture was then heated on a steam bath for one hour, allowed to stand at room temperature overnight (about fifteen hours) and then the solvent was distilled off in vacuo on a steam bath. To the residue was added 400 ml. of concentrated hydrochloric acid and 600 ml. of water and the mixture was slurried well. The mixture was extracted with three 600 ml. portions of chloroform. The aqueous layer was treated with decolorizing charcoal and filtered. The filtrate was made basic by adding aqueous ammonia and the oily product that separated was extracted with chloroform. The chloroform was distilled off in vacuo to yield 165.7 g. of an oily product, which consisted of a mixture of the three isomeric 4-, 3-, and 2-(3,4-dimethoxyphenyl)pyridines. These three isomers were separated by chromatography using 2 kg. of silica gel column set in a 2 l. sintered glass funnel successively using by volume 1:1 n-hexane-ether, ether alone and than 2% methanol in ether. Evaporation of the ether eluate yielded 67.8 g. of 2-(3,4-dimethoxyphenyl)pyridine, m.p. 76°–78° C. Evaporation of the 2% methanol-in-ether eluate yielded a mixture of the 3- and 4-isomers, 45.6 g., as a semi-solid, which was crystallized from ether to produce 24.8 g. of 4-(3,4-dimethoxyphenyl)pyridine, m.p. 101°–103° C. The mother liquor was combined with another faction which contained a mixture of 30.8 g. of the 2-, 3-, and 4-isomers as a red oil and the mixture was rechromatographed as above. There was then obtained another 15 g. of the 2-isomer and the remaining mixture, predominantly the 3-isomer, was dissolved in 6N HCl, 300 ml., and the solution treated with decolorizing charcoal. The filtrate was concentrated on a rotary-evaporator to yield a greenish residue, which was recrystallized from isopropyl alcohol to produce 33 g. of 3-(3,4-dimethoxyphenyl)pyridine hydrochloride, m.p. 198°–200° C.

EXAMPLE 2

3-(3,4-Dihydroxyphenyl)pyridine, alternatively named 4-(3-pyridinyl)-1,2-benzenediol - A solution containing 15 g. of 3-(3,4-dimethoxyphenyl)pyridine and 100 ml. of 48% hydrogen bromide was heated under reflux for thirty minutes and then allowed to stand at room temperature overnight. The resulting pale yellow crystalline precipitate was collected, washed with ethanol and dried in an oven at 80° C. to produce 14.3 g. of 3-(3,4-dihydroxyphenyl)pyridine hydrobromide, m.p. 288°–290° C. 3-(3,4-Dihydroxyphenyl)pyridine in free base form is obtained by treating an aqueous solution of the hydrobromide with an excess of aqueous sodium bicarbonate solution, collecting the resulting precipitate, washing it with water and drying it to produce 3-(3,4-dihydroxyphenyl)pyridine in free base form.

Other acid-addition salts of 3-(3,4-dihydroxyphenyl)pyridine are conveniently prepared by adding to a mixture of 1 g. of 3-(3,4-dihydroxyphenyl)pyridine in about 20 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring a molar equivalent quantities each of 3-(3,4-dihydroxyphenyl)pyridine and the appropriate acid, e.g., lactic acid or hydrochloric acid, to prepare respectively the lactate or hydrochloride salt of 3-(3,4-dihydroxyphenyl)pyridine in aqueous solution.

The following Example 3 is presented for comparative purposes. Neither this novel 2-(3,4-dihydroxyphenyl)pyridine nor the corresponding novel intermediate 2-(3,4-dimethoxyphenyl)pyridine shown above in the third paragraph of Example 1 are within the scope of the instantly claimed invention.

EXAMPLE 3

2-(3,4-Dihydroxyphenyl)pyridine as its hydrobromide, 4.1 g., m.p. 260°–262° C., was prepared following the procedure described in Example 1 using 4 g. of 2-(3,4-dimethoxyphenyl)pyridine, 35 ml. of 48% hydrogen bromide and a reflux period of three and one-half hours.

The usefulness of 4(or 3)-[3,4-di-(OR)-phenyl]pyridine or salt as cardiotonic agent is demonstrated by its effectiveness in standard pharmacological test procedures, for example, in causing a significant increase in the contractile force of the isolated cat atria and papillary muscle and in causing a significant increase in the cardiac contractile force in the anesthetized dog with low or minimal changes in heart rate and blood pressure. These test procedures are described in U.S. Pat. No. 4,072,746, issued Feb. 7, 1978.

When tested by the above-described isolated cat atria and papillary muscle procedure, 4(or 3)-[3,4-di-(OR)-phenyl]pyridine or salt at doses of 10, 30 and 100 $\mu$g./ml. was found to cause significant increase, that is, greater than 25%, in papillary muscle force and a significant increase, that is, greater than 25%, in right atrial force, while causing a lower percentage increase (than that of papillary muscle force and right atrial force) in right atrial rate. In contrast, the isomeric 2-(3,4-dihydroxyphenyl)pyridine hydrobromide (Example 3) was significantly less effective than its 3- and 4-isomers (Examples 1 and 2), showing only weak activity at only the highest dose tested (100 $\mu$g./ml.) whereas the 3- and 4-isomers showed significant activity at lower doses, i.e., 10 and 30 $\mu$g./ml.

When tested by said anesthetized dog procedure, 4-(3,4-dihydroxyphenyl)pyridine or salt when administered intravenously as a single bolus injection of 1, 3 and 10 mg./kg. caused a significant increase, that is, greater than 25%, in cardiac contractile force or cardiac contractility with correspondingly lower changes per dose in heart rate and blood pressure.

The present invention includes within its scope a cardiotonic composition for increasing cardiac contractility, said composition comprising a pharmaceutically-acceptable carrier and, as the active component thereof, the cardiotonic 4(or 3)-[3,4-di-(OR)-phenyl]pyridine or pharmaceutically-acceptable acid-addition salt thereof. The invention also includes within its scope the method for increasing cardiac contractility in a patient requiring such treatment which comprises administering to such patient an effective amount of said 4(or 3)-[3,4-di-(OR)-phenyl]pyridine or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavouring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 4(or 3)-(3,4-Dihydroxyphenyl)pyridine or pharmaceutically-acceptable acid-addition salt thereof.

2. 4-(3,4-Dihydroxyphenyl)pyridine or pharmaceutically-acceptable salt thereof.

3. A cardiotonic composition for increasing cardiac contractility, said composition comprising a pharmaceutically-acceptable inert carrier and, as the active component thereof, an effective amount of the cardiotonic 4(or 3)-[3,4-di-(OR)-phenyl]pyridine or pharmaceutically-acceptable acid-addition salt thereof, where R is hydrogen or methyl.

4. A composition according to claim 3 where the active component is 4-(3,4-dihydroxyphenyl)pyridine or pharmaceutically-acceptable salt thereof.

5. The method for increasing cardiac contractility in a patient requiring such treatment which comprises administering orally or parenterally in a solid or liquid dosage form to such patient an effective amount of the cardiotonic 4(or 3)-[3,4-di-(OR)-phenyl]pyridine or pharmaceutically-acceptable acid-addition salt thereof, where R is hydrogen or methyl.

* * * * *